US009629740B2

(12) United States Patent
Bouasaysy et al.

(10) Patent No.: US 9,629,740 B2
(45) Date of Patent: Apr. 25, 2017

(54) INFLATION DEVICES FOR INTRAGASTRIC DEVICES WITH IMPROVED ATTACHMENT AND DETACHMENT AND ASSOCIATED SYSTEMS AND METHODS

(75) Inventors: Outhit Bouasaysy, Corona, CA (US); Mark Ashby, Laguna Niguel, CA (US)

(73) Assignee: ReShape Medical, Inc., San Clemente, CA (US)

( * ) Notice: Subject to any disclaimer, the term of this patent is extended or adjusted under 35 U.S.C. 154(b) by 432 days.

(21) Appl. No.: 13/639,483

(22) PCT Filed: Apr. 6, 2011

(86) PCT No.: PCT/US2011/031463
§ 371 (c)(1),
(2), (4) Date: Feb. 4, 2013

(87) PCT Pub. No.: WO2011/127205
PCT Pub. Date: Oct. 13, 2011

(65) Prior Publication Data
US 2014/0031850 A1   Jan. 30, 2014

Related U.S. Application Data

(60) Provisional application No. 61/321,466, filed on Apr. 6, 2010.

(51) Int. Cl.
*A61F 5/00* (2006.01)
*A61L 2/23* (2006.01)

(52) U.S. Cl.
CPC ............ *A61F 5/0033* (2013.01); *A61F 5/003* (2013.01); *A61F 5/0036* (2013.01);
(Continued)

(58) Field of Classification Search
CPC ........ A61M 25/1025; A61M 25/10184; A61M 25/10185; A61M 25/10186; A61F 5/003; A61F 5/0033
See application file for complete search history.

(56) References Cited

U.S. PATENT DOCUMENTS 1,666,690 A   4/1928 Drevitson
1,690,995 A   11/1928 Pratt
(Continued)

FOREIGN PATENT DOCUMENTS

CA   2638988   5/2007
DE   8708978 U1   11/1987
(Continued)

OTHER PUBLICATIONS

European Search Report—Supplementary; EP 03726447.0, Applicant: Applied Medical Resources Corporation: Mar. 1, 2006, 3 pgs.
(Continued)

*Primary Examiner* — Thomas McEvoy
(74) *Attorney, Agent, or Firm* — Perkins Coie LLP

(57) ABSTRACT

Inflation devices for inflating intragastric devices and associated systems and methods are disclosed herein. In several embodiments, an inflation device can include a tube, an inner detent, and an outer detent. The tube can extend from a proximal portion of the inflation device to a distal portion of the inflation device, and can include a handle at the proximal portion and a barb at the distal portion. The barb can have a cross-sectional dimension greater than a cross-sectional dimension of a corresponding inflation port of an intragastric device. The inner detent can be positioned over the barb and can include a mating interface. The outer detent can be positioned over the inner detent, and can be configured to attach over a proximal cap of the intragastric device. The tube can be longitudinally advanceable relative to at least one of the inner and outer detents.

17 Claims, 8 Drawing Sheets

(52) U.S. Cl.
CPC .............. *A61F 5/0089* (2013.01); *A61L 2/23* (2013.01); *A61F 5/0043* (2013.01)

(56) References Cited

U.S. PATENT DOCUMENTS

| | | |
|---|---|---|
| 2,493,326 A | 1/1950 | Trinder |
| 2,579,301 A | 12/1951 | Buntin |
| 3,131,867 A | 5/1964 | Miller et al. |
| 4,133,315 A | 1/1979 | Berman et al. |
| 4,198,983 A | 4/1980 | Becker et al. |
| 4,246,893 A | 1/1981 | Berson |
| 4,281,582 A | 8/1981 | Jaqua |
| 4,356,824 A | 11/1982 | Vazquez |
| 4,368,739 A | 1/1983 | Nelson, Jr. |
| 4,416,267 A | 11/1983 | Garren et al. |
| 4,436,087 A | 3/1984 | Ouchi et al. |
| 4,465,072 A | 8/1984 | Taheri |
| 4,465,818 A | 8/1984 | Shirahata et al. |
| 4,485,805 A | 12/1984 | Foster, Jr. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 4,940,458 A | 7/1990 | Cohn |
| 5,073,347 A | 12/1991 | Garren et al. |
| 5,084,061 A | 1/1992 | Gau et al. |
| 5,123,840 A | 6/1992 | Nates |
| 5,234,454 A | 8/1993 | Bangs |
| 5,259,399 A | 11/1993 | Brown |
| 5,263,934 A | 11/1993 | Haak |
| 5,273,536 A | 12/1993 | Savas |
| 5,318,530 A | 6/1994 | Nelson, Jr. |
| 5,334,187 A | 8/1994 | Fischell et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith, III et al. |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A | 5/1999 | Daneshvar |
| 5,938,669 A | 8/1999 | Klaiber et al. |
| 5,976,073 A | 11/1999 | Ouchi |
| 5,993,473 A | 11/1999 | Chan et al. |
| 5,997,503 A | 12/1999 | Willis et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,283,951 B1 | 9/2001 | Flaherty et al. |
| 6,423,058 B1 | 7/2002 | Edwards et al. |
| 6,427,089 B1 | 7/2002 | Knowlton |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Silverman et al. |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,627 B2 | 3/2005 | Nozue et al. |
| 6,866,657 B2 | 3/2005 | Shchervinsky |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,942,680 B2 | 9/2005 | Grayzel et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,749,254 B2 | 7/2010 | Sobelman et al. |
| 7,828,749 B2 | 11/2010 | Douglas et al. |
| 7,829,572 B2 | 11/2010 | Didiuk et al. |
| 7,931,693 B2 | 4/2011 | Binmoeller et al. |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 9,149,611 B2 | 10/2015 | Bouasaysy |
| 2001/0022988 A1 | 9/2001 | Schwarz et al. |
| 2001/0037127 A1 | 11/2001 | De Hoyos Garza |
| 2002/0055757 A1 | 5/2002 | Torre et al. |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0186503 A1 | 9/2004 | DeLegge |
| 2004/0220665 A1 | 11/2004 | Hossainy et al. |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192614 A1 | 9/2005 | Binmoeller |
| 2005/0192615 A1 | 9/2005 | Torre et al. |
| 2005/0228504 A1 | 10/2005 | Demarais |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0058829 A1 | 3/2006 | Sampson et al. |
| 2006/0142700 A1 | 6/2006 | Sobelman et al. |
| 2006/0178691 A1 | 8/2006 | Binmoeller |
| 2006/0184112 A1 | 8/2006 | Horn et al. |
| 2006/0259020 A1 | 11/2006 | Sharratt |
| 2006/0270906 A1 | 11/2006 | Matsuno et al. |
| 2007/0016262 A1 | 1/2007 | Gross et al. |
| 2007/0078476 A1 | 4/2007 | Hull et al. |
| 2007/0083224 A1 | 4/2007 | Hively |

(56) References Cited

U.S. PATENT DOCUMENTS

| | | |
|---|---|---|
| 2007/0093728 A1 | 4/2007 | Douglas et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0118168 A1 | 5/2007 | Lointier et al. |
| 2007/0135829 A1 | 6/2007 | Paganon et al. |
| 2007/0142770 A1 | 6/2007 | Rioux et al. |
| 2007/0149994 A1 | 6/2007 | Sosnowski et al. |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0085887 A1 | 4/2008 | Didiuk et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208135 A1 | 8/2008 | Annunziata et al. |
| 2008/0208241 A1 | 8/2008 | Weiner et al. |
| 2008/0233167 A1 | 9/2008 | Li et al. |
| 2008/0243071 A1 | 10/2008 | Quijano et al. |
| 2008/0243166 A1 | 10/2008 | Paganon et al. |
| 2008/0255601 A1 | 10/2008 | Birk |
| 2008/0312679 A1 | 12/2008 | Hardert et al. |
| 2008/0319471 A1* | 12/2008 | Sosnowski et al. .......... 606/192 |
| 2009/0048624 A1 | 2/2009 | Alverdy |
| 2009/0250236 A1 | 10/2009 | Burnett et al. |
| 2009/0275973 A1 | 11/2009 | Chen et al. |
| 2009/0287231 A1 | 11/2009 | Brooks et al. |
| 2010/0023047 A1 | 1/2010 | Simpson |
| 2010/0049224 A1 | 2/2010 | Vargas |
| 2010/0063530 A1 | 3/2010 | Valencon et al. |
| 2010/0130998 A1 | 5/2010 | Alverdy |
| 2010/0174307 A1* | 7/2010 | Birk ................... A61F 5/003 606/192 |
| 2010/0191270 A1 | 7/2010 | Garza et al. |
| 2010/0234853 A1 | 9/2010 | Pecor et al. |
| 2010/0243135 A1 | 9/2010 | Pepper et al. |
| 2010/0251837 A1 | 10/2010 | Bouasaysy et al. |
| 2011/0172767 A1 | 7/2011 | Rathi et al. |
| 2011/0178544 A1 | 7/2011 | Sosnowski et al. |
| 2011/0276076 A1 | 11/2011 | Paganon |
| 2011/0295300 A1 | 12/2011 | Verd et al. |
| 2012/0191126 A1 | 7/2012 | Pecor et al. |
| 2012/0271336 A1 | 10/2012 | Hamman et al. |
| 2012/0271338 A1 | 10/2012 | Bouasaysy et al. |
| 2012/0289992 A1 | 11/2012 | Quijano et al. |
| 2013/0035710 A1 | 2/2013 | Bouasaysy et al. |
| 2013/0053880 A1 | 2/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0257358 A1 | 9/2014 | Alverdy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor et al. |
| 2015/0366691 A1 | 12/2015 | Bouasaysy et al. |
| 2016/0008156 A1 | 1/2016 | Pecor et al. |

FOREIGN PATENT DOCUMENTS

| | | |
|---|---|---|
| EP | 0103481 | 3/1984 |
| EP | 0457456 A1 | 11/1991 |
| EP | 0485903 A2 | 5/1992 |
| EP | 1781183 | 5/2007 |
| FR | 2862525 A1 | 5/2005 |
| FR | 2892297 | 4/2007 |
| GB | 2090747 A | 7/1982 |
| GB | 2139902 A | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| JP | 2009285135 A | 12/2009 |
| JP | 2015154964 | 8/2015 |
| JP | 2016127954 | 7/2016 |
| WO | 8805671 A1 | 8/1988 |
| WO | 9000369 A1 | 1/1990 |
| WO | 9925418 A1 | 5/1999 |
| WO | WO-0141700 | 6/2001 |
| WO | WO-0166166 A2 | 9/2001 |
| WO | WO-0240081 | 5/2002 |
| WO | 2005082296 A1 | 9/2005 |
| WO | 2005107641 A2 | 11/2005 |
| WO | 2005120363 A1 | 12/2005 |
| WO | WO-2006035446 A2 | 4/2006 |
| WO | WO-2006056944 A1 | 6/2006 |
| WO | WO-2006/128978 A1 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009055386 A2 | 4/2009 |
| WO | WO-2009112786 A2 | 9/2009 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011024077 A2 | 3/2011 |
| WO | WO-2011038270 A2 | 3/2011 |
| WO | WO-2011097637 A1 | 8/2011 |
| WO | WO-2011127205 A1 | 10/2011 |
| WO | WO-2012048226 A1 | 4/2012 |

OTHER PUBLICATIONS

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043134; Applicant: ReShape Medical, Inc., Mailing Date Apr. 27, 2011, 12 pages.

International Search Report; International Application No. PCT/US2010/043136; Applicant: ReShape Medical, Inc., Mailing Date Apr. 12, 2011, 9 pages.

International Search Report; International Application No. PCT/US2010/050260; Applicant: ReShape Medical, Inc., Mailing Date: Jun. 17, 2011, 9 pages.

International Search Report; International Application No. PCT/US2011/026233; Applicant: ReShape Medical, Inc., Mailing Date Apr. 26, 2011, 9 pages.

International Search Report; International Application No. PCT/US2011/031463; Applicant: ReShape Medical, Inc., Mailing Date: Jun. 27, 2011, 10 pages.

International Search Report; International Application No. PCT/US2003/012782, Applicant: Applied Medical Resources Corporation, dated: Oct. 28, 2003, 7 pages.

International Search Report; International Application No. PCT/US2006/042336, Applicant: Abdominus, Inc., dated: Mar. 14, 2007, 9 pages.

International Search Report; International Application No. PCT/US2006/042710, Applicant: Abdominus, Inc. et al., dated: Mar. 15, 2007, 9 pages.

International Search Report; International Application No. PCT/US2006/042711, Applicant: Abdominus, Inc. et al., dated: Mar. 16, 2007, 9 pages.

(56) References Cited

OTHER PUBLICATIONS

International Search Report; International Application No. PCT/US2006/048647, Applicant: Abdominus, Inc. et al., dated: May 22, 2007, 12 pages.
International Search Report; International Application No. PCT/US2008/058677, Applicant: ReShape Medical et al., dated: Aug. 21, 2008, 12 pages.
International Search Report; International Application No. PCT/US2008/068058, Applicant: ReShape Medical, Inc. et al, dated: Nov. 19, 2008, 11 pages.
International Searbh Report; International Application No. PCT/US2010/029865, Applicant: ReShape Medical, Inc., dated: Jan. 5, 2011, 9 pages.
International Search Report; International Application No. PCT/US2011/024077; Applicant: ReShape Medical, Inc., dated: Apr. 6, 2011, 12 pages.
International Search Report; International Application No. PCT/US2011/024082, Applicant: ReShape Medical, Inc., dated: Apr. 6, 2011, 10 pages.
International Search Report; International Application No. PCT/US1155373, Applicant: Reshape Medical, Inc., dated: Jan. 20, 2012, 7 pages.
"Living with the BIB: BioEnterics Intragastric Balloon Program: Patient Information"; INAMED Health: Bioenteris Corporation, ECO-SBA-10434; dated Apr. 20, 2004 and May 14, 2005, located online at: www.sydneyobesity.com.au/pdf/M946-01.pdf; 10 pages.
Non-Final Office Action; U.S. Appl. No. 11/263,302; dated: Oct. 9, 2012, 6 pages.
Non-Final Office Action; U.S. Appl. No. 11/694,536; dated: Oct. 26, 2011, 13 pages.
Non-Final Office Action; U.S. Appl. No. 12/723,545; dated Feb. 29, 2012, 10 pages.
Non-Final Office Action; U.S. Appl. No. 12/625,473; dated Oct. 24, 2011, 18 pages.
Non-Final Office Action; U.S. Appl. No. 12/625,473; dated Jul. 12, 2012; 10 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
ReShape Inflatable Gastric Balloon Going on Trial as Weight Loss Option, MedGadget: Internet Journal of Emerging Medical Technologies. Feb. 4, 2010, 5 pages.
Wahlen CH et al. "The BioEnterics Intragastric Balloon: How to use it" Obesity Surgery 2001; 11:524-527.
Extended European Search Report; Application No. EP11748141.6, Applicant: Reshape Medical, Inc., mailed Feb. 25, 2014, 6 pages.
Final Office Action; U.S. Appl. No. 13/858,767, Mailing Date May 22, 2103, 12 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,8-32, mailed on Jan. 28, 2014, 8 pages.
Non-Final Office Action; U.S. Appl. No. 13/386,650; mailed on Jun. 3, 2014, 15 pages.
Notice of Allowance; U.S. Appl. No. 12/753,803, dated May 13, 2014, 18 pages.
Ostrovsky, ReShape Inflatable Gastric Balloon going on Trial as Weight Loss Option; http://www.medgadget.com/2010/02/reshape_inflatable_gastric_balloon_system_going_on_trial_as_wieight_loss_option.html Feb. 4, 2010, retrieved on Feb. 10-2-13.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
Extended European Search Report; Application No. EP6827098.3, Applicant: Reshape Medical, Corporation, mailed on Aug. 25, 2014, 3 pages.
Extended European Search Report; Application No. EP6827314.3, Applicant: ReShape Medical Corporation, mailed on Aug. 1, 2014, 3 pages.
Extended European Search Report; Application No. EP6827313.5, Applicant: ReShape Medical Corporation, mailed on Jul. 30, 2014, 5 pages.
Extended European Search Report; Application No. EP6847847.8, Applicant: ReShape Medical Corporation, mailed on Aug. 14, 2014, 5 pages.
Final Office Action; U.S. Appl. No. 13/858,767, mailed on May 30, 2014, 12 pages.
Non-Final Office Action; U.S. Appl. No. 13/386,638, mailed on Jun. 27, 2014, 12 pages.
Extended European Search Report; Application No. EP11766679.2, Applicant Reshape Medical, Inc., mailed Dec. 12, 2013, 6 pages.
Cronin, Carmel G. et al., "Normal small bowel wall characteristics on MR enterography," *European Journal of Radiology* 74(2):207-211, Aug. 2010.
Gray, Henry, Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Partial Supplementary European Search Report for European Application No. 11740535.7, Applicant: ReShape Medical, Inc., mailed Oct. 20, 2015, 7 pages.
Final Office Action for Japanese Application No. 2014-52972, Applicant: ReShape Medical, Inc., mailed on Oct. 9, 2015, 8 pages.
Canadian Office Action; Application No. CA 2638163, Applicant: Reshape Medical, Inc., mailed Dec. 8, 2015, 4 pages.
Canadian 2nd Office Action Application No. 2680124, Applicant: ReShape Medical, Inc., mailed Jul. 9, 2015, 3 pages.
European Examination Report; Application No. 06827313.5, Applicant: ReShape Medical Inc., mailed Jul. 13, 2015, 5 pages.
European Examination Report; Application No. 06847847.8, Applicant: ReShape Medical Inc., mailed Jul. 13, 2015, 4 pages.
Japanese Office Action; Application No. 2013-532976; Applicant: ReShape Medical, Inc., mailed Jun. 26, 2015, 10 pages.
Canadian Office Action: Application No. CA 2680124, Applicant: Reshape Medical Corporation, mailed Nov. 4, 2014, 3 pages.
Canadian Office Action; Application No. 2,691,530, mailed Dec. 18, 2014, 4 pages.
Canadian Office Action; Application No. CA 2638163, Applicant: Reshape Medical Corporation, mailed Mar. 10, 2015, 4 pages.
Canadian Office Action; Application No. CA 2638988, Applicant Reshape Medical Corporation, mailed Dec. 22, 2014 3 pages.
Canadian Office Action; Application No. CA 2638988, Applicant Reshape Medical Corporation, mailed Mar. 6, 2014, 4 pages.
Canadian Office Action; Application No. CA 2638989, Applicant: Reshape Medical Corporation, mailed May 22, 2013 3 pages.
Canadian Office Action; Application No. CA 2640554, Applicant: Reshape Medical Corporation, mailed May 27, 2013, 2 pages.
Canadian Office Action; Application No. CA2484838, Applicant: Reshape Medical, Inc., mailed Nov. 13, 2009, 3 pages.
Canadian Office Action; Application No. CA2484838, Applicant: Reshape Medical, Inc., mailed Sep. 24, 2010, 3 pages.
Canadian Office Action; Application No. CA2638163, Applicant: Reshape Medical Corporation, mailed Jul. 17, 2013, 2 pages.
Canadian Office Action; Application No. CA2638988, Applicant: Reshape Medical Corporation, mailed May 28, 2013, 3 pages.
Canadian Office Action; Application No. CA2780085, Applicant: Reshape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. EP108002918.2, Applicant: Reshape Medical Inc., mailed Dec. 17, 2014, 5 pages.
European Examination Report; Application No. EP108029943, Applicant: Reshape Medical Inc., mailed Dec. 18, 2014, 4 pages.
European Examination Reported; Application No. 08771842.5, May 7, 2015, 5 pages.

(56) References Cited

OTHER PUBLICATIONS

European Supplementary Search Report; Application No. 08771842.5, Apr. 24, 2015, 3 pages.
Extended European Search Report; Application No. 08732989.2, Applicant: Reshape Medical, Inc., mailed Oct. 16, 2014, 7 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application No. JP2013-43712, mailed Jan. 8, 2015, 8 pages.
Japanese Office Action; Application. No. JP2013-043712, mailed Apr. 22, 2013, 5 pages.
Chou, Chyuan et al., "Structural Effects On The Thermal Properties Of PDPS/PDMS Copolymers," Journal of Thermal Analysis, vol. 40, pp. 657-667, 1993.
European Search Report for European Application No. 11740535.7, Applicant: ReShape Medical, Inc., mailed Mar. 8, 2016, 14 pages.
Extended European Search Report; Application No. 15198773.2, Application ReShape Medical Corporation, mailed Jul. 15, 2016, 7 pages.
European Examination Report; Application No. 11766679.2, Applicant: Reshape Medical Inc., mailed Dec. 1, 2016, 4 pages.
European Examination Report; Application No. 11748141.6, Applicant: Reshape Medical Inc., mailed Dec. 8, 2016, 3 pages.
Extended European Search Report; Application No. 16183882.6, Applicant: Reshape Medical Inc., mailed Feb. 17, 2017, 9 pages.

* cited by examiner

INFLATION DEVICES FOR INTRAGASTRIC DEVICES WITH IMPROVED ATTACHMENT AND DETACHMENT AND ASSOCIATED SYSTEMS AND METHODS

CROSS-REFERENCE TO RELATED APPLICATION(S)

The present application is a U.S. National Phase application under 35 U.S.C. 371 of International Application Serial No. PCT/US2011/031463, filed Apr. 6, 2011, which claims the benefit of U.S. Provisional Patent Application Ser. No. 61/321,466, filed Apr. 6, 2010, the entire contents of which are incorporated herein by reference in their entireties.

RELATED REFERENCES

This application incorporates by reference in their entirety each of the following applications and publications: U.S. patent application Ser. No. 11/768,152, filed Jun. 25, 2007, entitled GASTRIC SPACE FILLER DEVICE, DELIVERY SYSTEM, AND RELATED METHODS; U.S. patent application Ser. No. 11/263,302, filed Oct. 31, 2005, entitled INTRAGASTRIC SPACE FILLER; U.S. Pat. Pub. No. 2007/0100367, published May 3, 2007, entitled INTRAGASTRIC SPACE FILLER; U.S. Pat. Pub. No. 2007/0100368, published May 3, 2007, entitled INTRAGASTRIC SPACE FILLER; U.S. Pat. Pub. No. 2007/0100369, published May 3, 2007, entitled INTRAGASTRIC SPACE FILLER; U.S. Pat. Pub. No. 2007/0149994, published Jun. 28, 2007, entitled INTRAGASTRIC SPACE FILLER AND METHODS OF MANUFACTURE; U.S. Pat. Pub. No. 2008/0243071, published Oct. 2, 2008, entitled INTRAGASTRIC BALLOON SYSTEM AND THERAPEUTIC PROCESSES AND PRODUCTS; U.S. Pat. Pub. No. 2008/0319471, published Dec. 25, 2008, entitled GASTRIC SPACE FILLER DEVICE, DELIVERY SYSTEM, AND RELATED METHODS; U.S. Pat. Pub. No. 2005/0159769, published Jul. 21, 2005, entitled BALLOON SYSTEM AND METHODS FOR TREATING OBESITY; U.S. Pat. Pub. No. 2009/0048624, published Feb. 19, 2009, entitled BALLOON SYSTEM AND METHODS FOR TREATING OBESITY; WIPO Pub. No. WO 2007/053556, published Oct. 5, 2007, entitled INTRAGASTRIC SPACE FILLER; WIPO Pub. No. WO 2007/053707, published Oct. 5, 2007, entitled INTRAGASTRIC SPACE FILLER; WIPO Pub. No. WO 2007/053706, published Oct. 5, 2007, entitled INTRAGASTRIC SPACE FILLER; and WIPO Pub. No. WO 2007/075810, published May 7, 2007, entitled INTRAGASTRIC SPACE FILLER.

TECHNICAL FIELD

The present technology relates generally to implantable gastric devices. In particular, the present technology relates to inflation devices for implanting and inflating an intragastric device in situ and associated systems and methods.

BACKGROUND

Implantable gastric devices can occupy a volume within a patient's stomach to decrease the available room for food. This creates a feeling of satiety that can control the patient's appetite and cause weight loss. Intragastric balloons, for example, can be filled with a biocompatible fluid (e.g., saline solution) and left within the stomach for an extended period of time to treat obesity and/or other weight related conditions. Implanting such an intragastric balloon generally includes inserting the deflated balloon through the patient's mouth or nose with a filler tube or catheter, and inflating the balloon in situ. The intragastric balloon can eventually be removed by deflating the balloon, grasping it with an extraction tool, and removing the intragastric balloon via the esophagus and mouth.

A challenge associated with the inflation of intragastric balloons is that conventional inflation tools can inadvertently disconnect from the intragastric balloons during insertion and/or inflation. However, if it is difficult to disconnect the intragastric balloon from the inflation tools, the extra force (e.g., tugging) necessary for disengagement can agitate or impose trauma on the stomach wall. Thus, there is a need to improve the inflation of intragastric devices.

DETAILED DESCRIPTION

Specific details of several embodiments of the present technology are described below with reference to an inflation device for an intragastric device and associated methods for inflating, implanting, and explanting such devices. Although many of the embodiments are described below with respect to a dual balloon intragastric device, other embodiments of intragastric devices can include only one balloon or more than two balloons. Moreover, several further embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1-13.

The terms "distal" and "proximal" within this application reference a relative position of portions of an intragastric device and/or an inflation device with reference to an operator. Proximal refers to a position closer to the operator of the device, and distal refers to a position that is more distant from the operator of the device.

Figure 1:
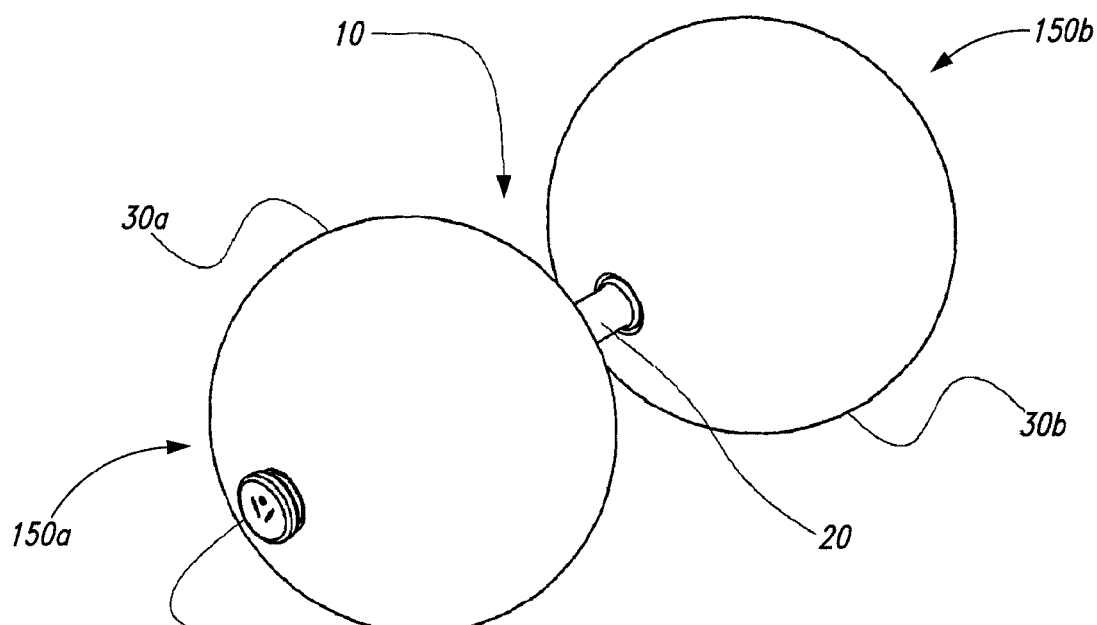
FIG. 1 is a schematic isometric view of an intragastric device in accordance with an embodiment of the present technology.
Figure 2:
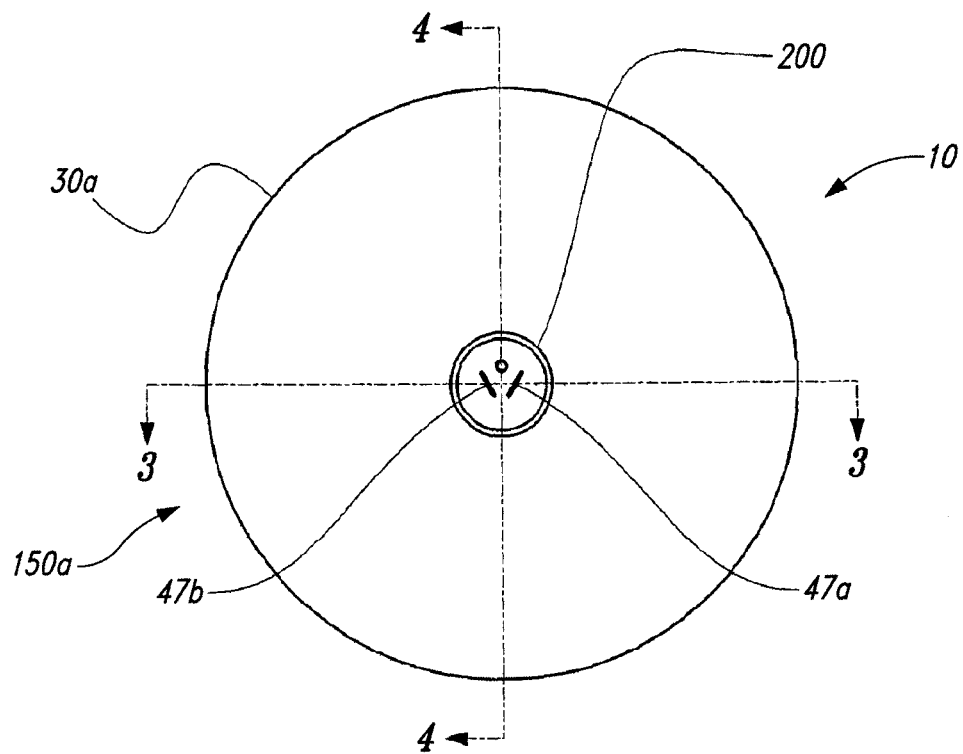
FIG. 2 is a schematic top view of the intragastric device of FIG. 1.

FIG. 1 is an isometric view of an intragastric device 10 in accordance with an embodiment of the present technology, and FIG. 2 is a top view of the intragastric device 10 of FIG. 1. The intragastric device 10 may include at least one expandable, space-filling component, such as a balloon 30. As shown in FIG. 1, the intragastric device 10 can include a first balloon 30a and a second balloon 30b fixed to a shaft 20. In other embodiments, the intragastric device 10 can include additional balloons 30. As shown in FIGS. 1 and 2, the intragastric device 10 may also include or be configured to interface with a proximal cap 200 at a proximal portion 150a of the intragastric device 10.

Figure 3:
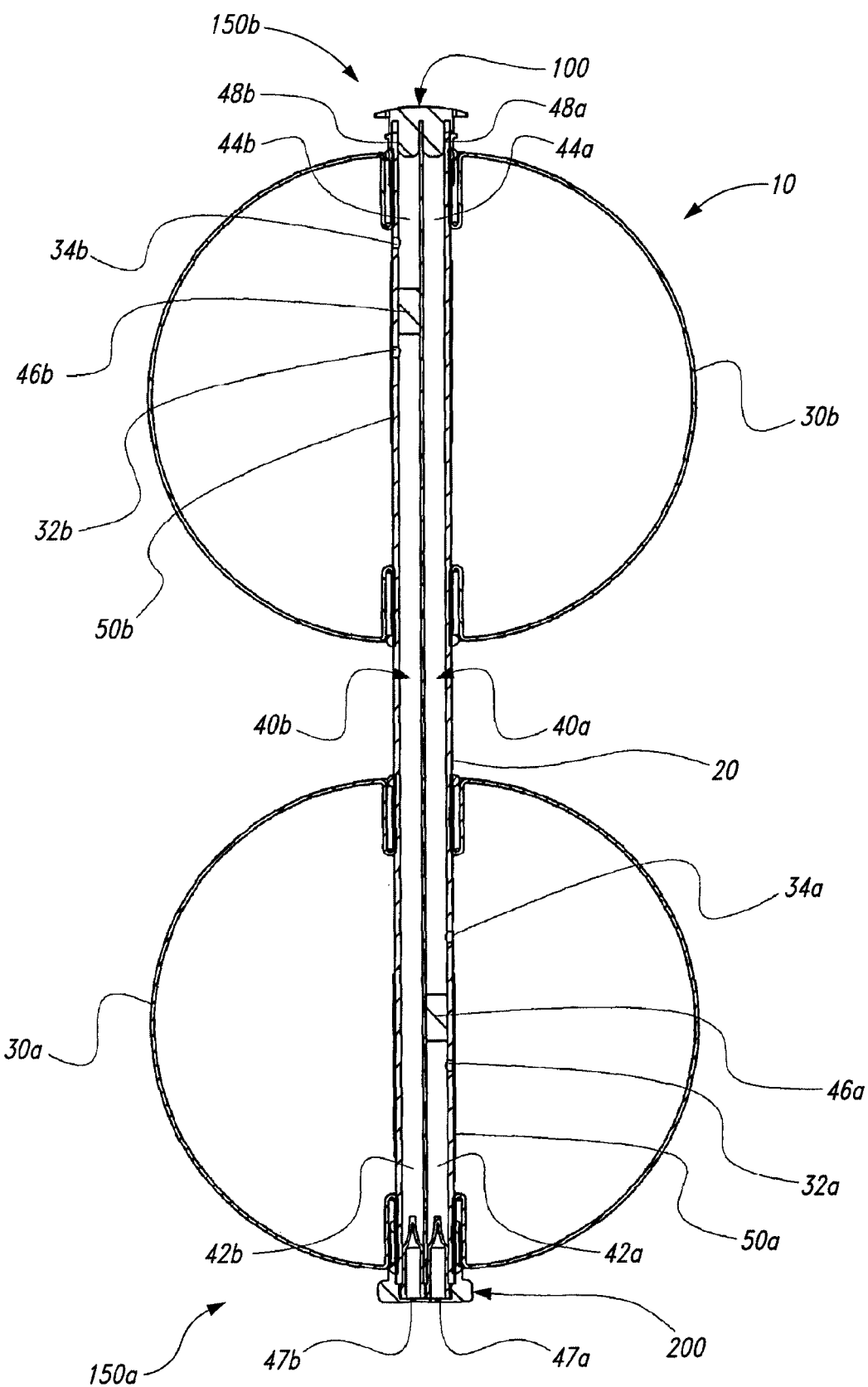
FIG. 3 is a schematic cross-sectional view of the intragastric device taken substantially along the line 3-3 of FIG. 2.

FIG. 3 is a cross-sectional view of the intragastric device 10 taken substantially along the line 3-3 of FIG. 2. As shown in FIG. 3, the shaft 20 of the intragastric device 10 may include a plurality of lumens 40 (identified individually as a first lumen 40a and a second lumen 40b), each corresponding to a balloon 30 of the intragastric device 10. For example, the first lumen 40a may provide fluid communication from a first inflation port 47a to an interior portion of the first balloon 30a via a first inflation opening 32a. Likewise, the second lumen 40b may provide fluid communication from a second inflation port 47b to an interior portion of the second balloon 30b via a second inflation opening 33b.

Each lumen 40 may have a corresponding inflation port 47 at a proximal end thereof. The inflation ports 47 may be configured to allow infusion of fluids into corresponding lumens 40 and inhibit or prevent the exit of fluids from the same. The inflation ports 47 may include check valves, clack valves, non-return valves, one-way valves, duckbill valves, reed valves, flapper valves, etc. For example, the first inflation port 47a may be provided at a proximal end of the first lumen 40a. Likewise, the second inflation port 47b may be provided at a proximal end of the second lumen 40b.

As shown in FIG. 3, each lumen 40 of the shaft 20 may be divided into inflation chambers 42 (identified individually as a first inflation chamber 42a and a second inflation chamber 43b) and aspiration chambers (identified individually as a first aspiration chamber 44a and a second aspiration chamber 44b). For example, the first lumen 40a may be divided into the first inflation chamber 42a and the first aspiration chamber 44a by a first barrier 46a. Similarly, the second lumen 40b may be divided into the second inflation chamber 43b and the second aspiration chamber 44b by a second barrier 46b. Such barriers 46 may partition the lumens 40 into at least two separate chambers that may be fluidly connected via the interior portion of a corresponding balloon 30.

Each balloon 30 may have an opening that fluidly connects the interior portion of the balloon 30 with at least a portion of the corresponding lumen 40. As shown in FIG. 3, each balloon 30 can have a plurality of openings that connect the interior portion of the balloon 30 with disparate chambers (e.g., the inflation chambers 42, the aspiration chambers 44) of the corresponding lumen 40. For example, a first inflation opening 32a may provide a fluid connection between the interior of the first balloon 30a and the first inflation chamber 42a, and a first aspiration opening 34a may provide a fluid connection between the interior of the first balloon 30a and the first aspiration chamber 44a. Similarly, a second inflation opening 33b may provide a fluid connection between the interior of the second balloon 30b and the second inflation chamber 43b, and a second aspiration opening 34b may provide a fluid connection between the interior of the second balloon 30b and the second aspiration chamber 44b.

As further shown in FIG. 3, the intragastric device 10 can include sleeves 50 (identified individually as a first sleeve 50a and a second sleeve 50b) within the interior of the balloons 30 that cover the inflation openings 32. Such sleeves 50 may allow inflation of the balloon from the corresponding inflation opening 32 while inhibiting or preventing deflation through the same opening 32. The sleeves 50 may wrap radially around the portion of the shaft 20 with compression force near the corresponding opening 32. For example, the first sleeve 50a may be provided within the interior portion of the first balloon 30a and cover at least the first inflation opening 32a. Similarly, the second sleeve 50b may be provided within the interior portion of the second balloon 30b and cover at least the second inflation opening 33b. The sleeve 50 may inhibit or prevent undesirable fluid passage through the inflation openings 32, and thereby reduce fluid leakage from inflated balloons 30 and associated issues. For example, when pressure within the balloon 30 exceeds pressure in the corresponding inflation chamber 42, the sleeve 50 may be pressed with radial compression against the corresponding inflation opening 32 to inhibit or prevent leakage into the lumen 40. When pressure within the inflation chamber 42 exceeds pressure within the corresponding balloon 30, the sleeve 50 may separate from the corresponding inflation opening 32 and permit fluid passage through the inflation opening 32 into the balloon 30.

Additionally, as shown in FIG. 3, each lumen 40 may have a corresponding aspiration port 48 (identified individually as a first aspiration port 48a and a second aspiration port 48b) formed by the opening at the distal end thereof. The aspiration ports 48 may be selectively covered by a sealing device 100. For example, the first aspiration port 48a may be at a distal end of the first lumen 40a. Similarly, the second aspiration port 48b may be provided at a distal end of the second lumen 40b.

Figure 4:
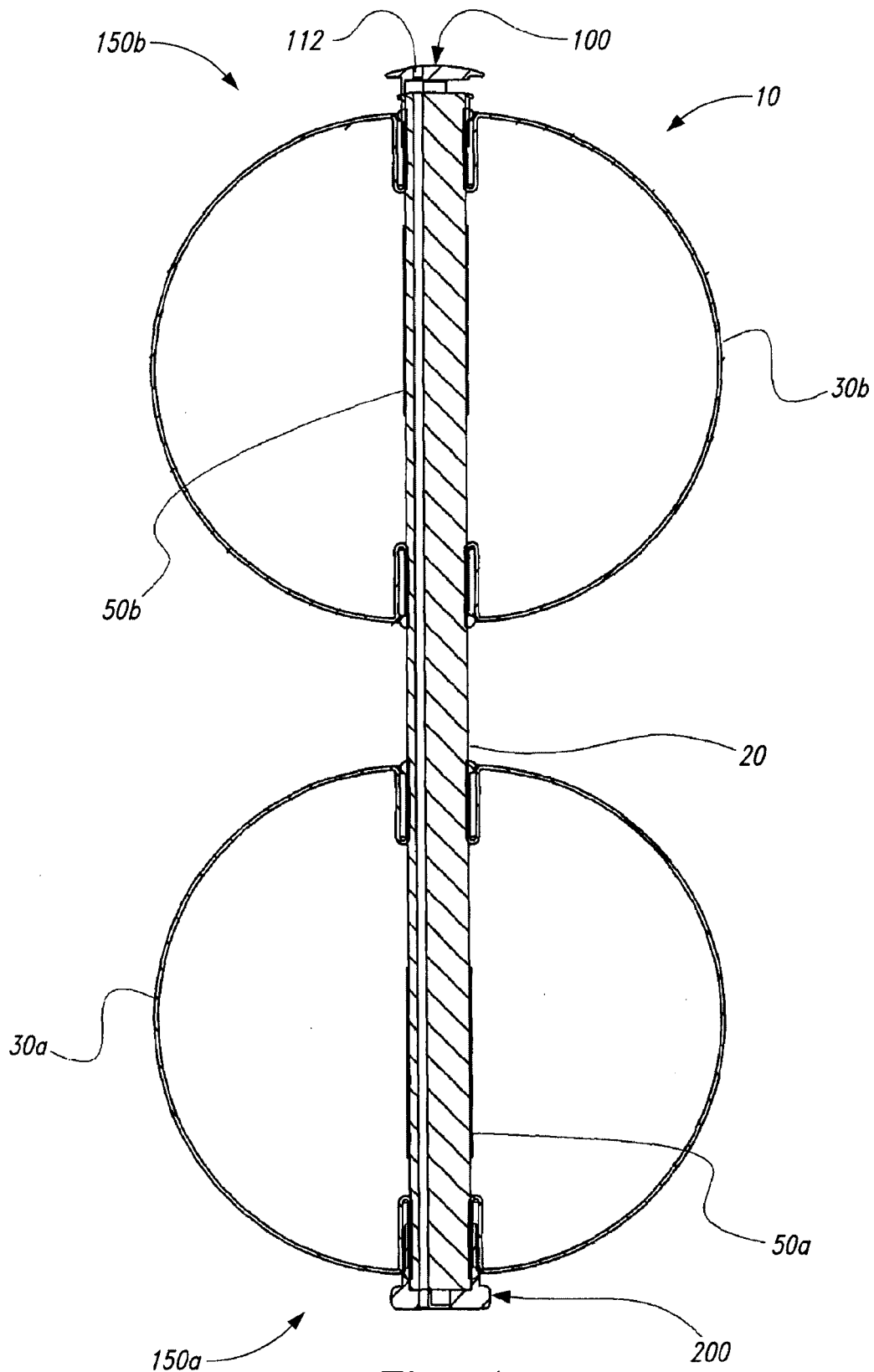
FIG. 4 is a schematic cross-sectional view of the intragastric device taken along line 4-4 of FIG. 2.

FIG. 4 is a cross-sectional view of the intragastric device 10 taken substantially along the line 4-4 of FIG. 2. In the illustrated embodiment, a guidewire channel 112 may extend through the sealing device 100, the proximal cap 200, and the shaft 20 of the intragastric device 10. The guidewire channel 112 may be configured to accommodate a guidewire for assisted delivery and management of the intragastric device 10 during implant, explant, or maintenance thereof.

Figure 5:
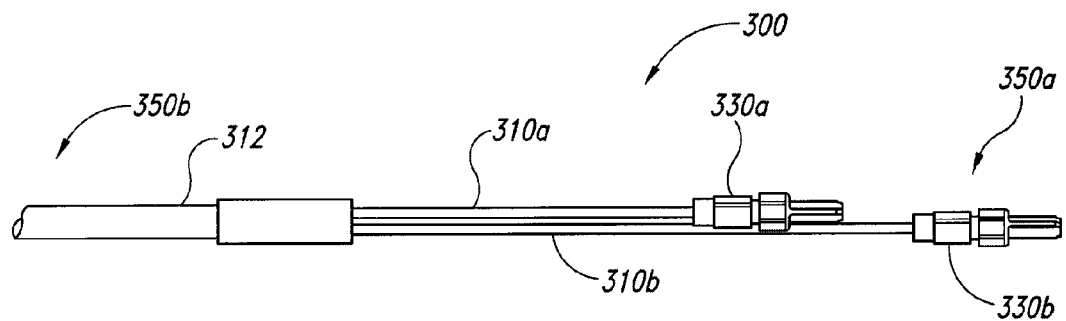
FIG. 5 is a top view of a proximal portion of an inflation device in accordance with an embodiment of the present technology.
Figure 7:
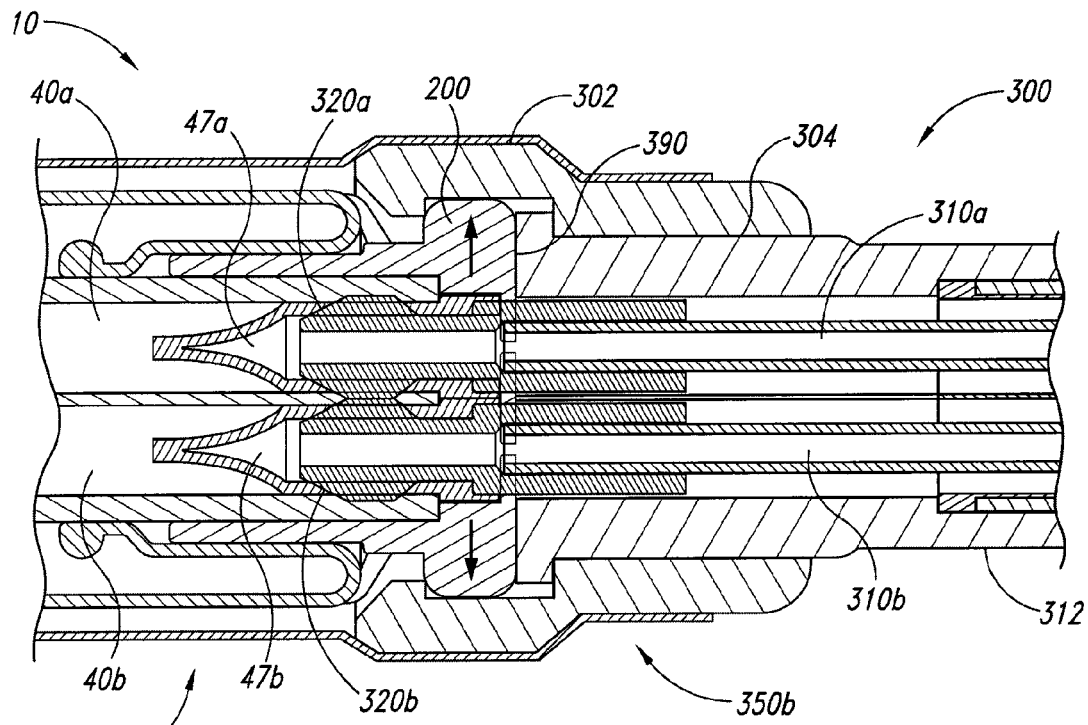
FIG. 7 is a cut-away view of an inflation device engaged with an intragastric device in accordance with an embodiment of the present technology.

FIG. 5 is a top view of a proximal portion 350 of an inflation device 300 in accordance with an embodiment of the present technology. The inflation device 300 may be provided for delivery and inflation of the intragastric device 10 (FIGS. 1-4) in situ. As shown in FIG. 5, at a proximal portion 350a, the inflation device 300 may include tubes 310 (identified individually as a first tube 310a and a second tube 310b) corresponding to each balloon 30 of the intragastric device 10. For example, the first tube 310a may mechanically and fluidly connect a first handle 330a to a first barb 320a (FIG. 7), and the second tube 310b may mechanically and fluidly connect a second handle 330b to a second barb 320b (FIG. 7). Longitudinal advancement and retraction of the first barb 320a and the second barb 320b may be actuated by a user operating the first handle 330a and the second handle 330b at the proximal portion 350a of the inflation device 300. As further shown in FIG. 5, the tubes 310 can be enclosed, contained, and/or otherwise stored at least partially within a housing 312. In other embodiments, the inflation device 300 does not include the housing 312.

Figure 6:
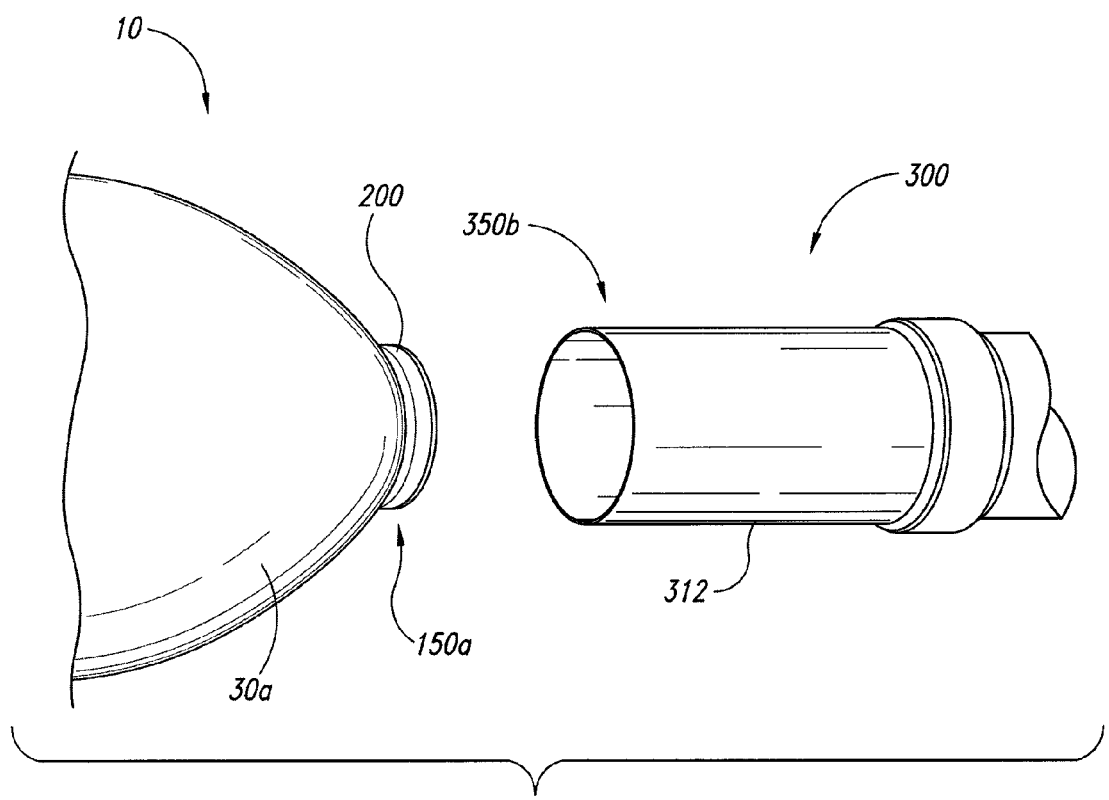
FIG. 6 is a top view of a proximal portion of an intragastric device and a distal portion of the inflation device of FIG. 5.

FIG. 6 is a top view of the proximal portion 150 of the intragastric device 10 of FIGS. 1-4 and the distal portion 350b of the inflation device 300 of FIG. 5. As shown in FIG. 6, the distal portion 350b of the inflation device 300 may be configured to mate with the proximal cap 200 of the intragastric device 10. Advancement, retraction, and positioning of barbs 320 (FIG. 7) may be sensed by a user holding a corresponding handle 330. Inflation of at least one of the first balloon 30a and the second balloon 30b can occur while the inflation device 300 is mated with the proximal cap 200 of the intragastric device 10.

FIG. 7 is a cut-away view of the inflation device 300 of FIGS. 5 and 6 engaged with the intragastric device 10 of FIGS. 1-4 in accordance with an embodiment of the present technology. As shown in FIG. 7, the inflation device 300 may include at least one of an outer detent 302 and an inner detent 304. The outer detent 302 and the inner detent 304 may be separate pieces or separate portions of the same integral piece. The outer detent 302 may mate around or over a distal portion (e.g., flared/flanged section) of the proximal cap 200. In selected embodiments, the outer detent 302 can be elastic such that the outer detent 302 can shrink when removed from the proximal cap 200 for a lower safety profile. In other embodiments, the outer detent 302 can be rigid or non-elastic (e.g., a fiber hoop) and configured to collapse. Whether elastic or non-elastic, the large outer detent 302 provides retention forces and stability that is generally higher than an internal fixed flange of a smaller diameter (e.g., as with a flanged attachment of the BIB device). Additionally, when collapsed, the outer detent 302 takes up less space in the esophagus to enable simultaneous retraction of both an associated catheter and scope, or serial retraction of both components.

The inner detent 304 may mate against a proximal portion of the proximal cap 200. Before, during, or after such mating, the first barb 320a may be inserted into the first inflation port 47a to provide fluid to the first lumen 40a, and the second barb 320b may be inserted into the second inflation port 47b to provide fluid to the second lumen 40b. In the embodiment illustrated in FIG. 7, the mating interface 390 is a flat surface. In other embodiments, the mating interface 390 can include ridges, beveled edges, filleted edges, and/or other non-planar surfaces.

As shown in FIG. 7, the first barb 320a and the second barb 320b may be longitudinally advanceable relative to at least one of the outer detent 302 and the inner detent 304. At least a portion of the first barb 320a and/or the second barb 320b may have a diameter or cross-sectional area that exceeds the diameter or cross-sectional area of at least a portion of the corresponding inflation port 47 in an unengaged state. Accordingly, insertion of the first barb 320a into the first inflation port 47a or the second barb 320b into the second inflation port 47b may cause expansion of the proximal cap 200 in an engaged state. As indicated by the arrows in FIG. 7, the expansion of the proximal cap 200 may be radially outward. The proximal cap 200 can also expand in other directions (e.g., toward the inner detent 304). Such expansion may reduce the ease with which the outer detent 302 may disengage from the proximal cap 200. For example, engaging the outer detent 302 around the proximal cap 200 may be made more secure by the expansion of the proximal cap 200 such that the force required to disengage the outer detent 302 from the proximal cap 200 is greater when one or both of the barbs 320 are engaged within the corresponding inflation port 47. Accordingly, the force required to disengage the outer detent 302 from the proximal cap 200 is lower when one or both of the barbs 320 are disengaged from the corresponding inflation ports 47.

Figure 8:
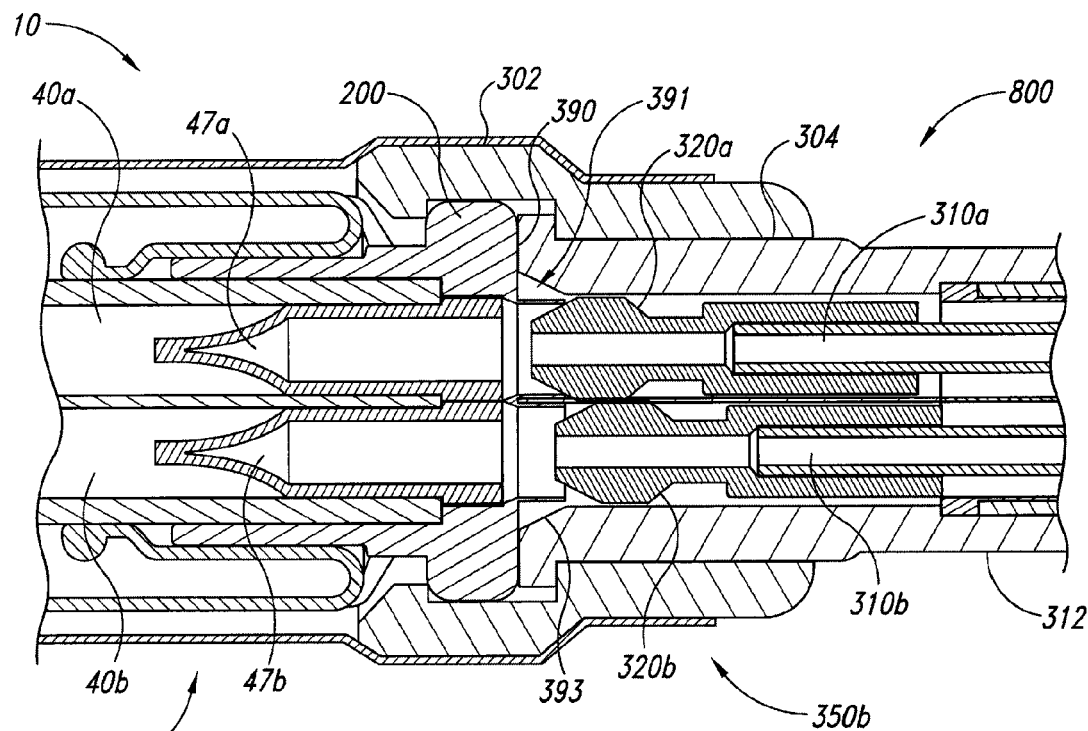
FIG. 8 is a cut-away view of an inflation device and an intragastric device in accordance with another embodiment of the present technology.

FIG. 8 is a cut-away view of an inflation device 800 and the intragastric device 10 in accordance with another embodiment of the present technology. The inflation device 800 includes features generally similar to the inflation device 300 described above with reference to FIGS. 5-7. For example, the inflation device 800 can include the tubes 310 connected to the barbs 320, the outer detent 302, and the inner detent 304. The inner detent 304 can also include the mating interface 390. As shown in FIG. 8, the mating interface 390 can be configured to leave an open space 391 near the proximal cap 200 when the inflation device 800 and the proximal cap 200 are engaged. The open space 391 can be defined by the mating interface 390 and the proximal cap 200. For example, in the embodiment illustrated in FIG. 8, the open space 391 is defined by a chamfered portion 393 of the mating interface 390 and the proximal cap 200. In other embodiments, the mating interface 390 can include scallops, ridges, and/or other cut-outs with different shapes and geometries that leave one or more open spaces 391 near the proximal cap 200.

The open space 391 may provide a channel into which the proximal cap 200 may expand. For example, insertion of at least one of the barbs 320 into the corresponding inflation ports 47 may cause expansion of the proximal cap 200. At least some of the expansion of the proximal cap 200 may occur into the open space 391 rather than against the outer detent 302. The distribution of this expansion may increase the force required to disengage the outer detent 302 from the proximal cap 200, further allowing the proximal cap material to deflect when the barbs 320 are retracted. This allows a user to selectively reduce the engagement force of the outer 302 detent to the proximal cap 200.

Figure 9:
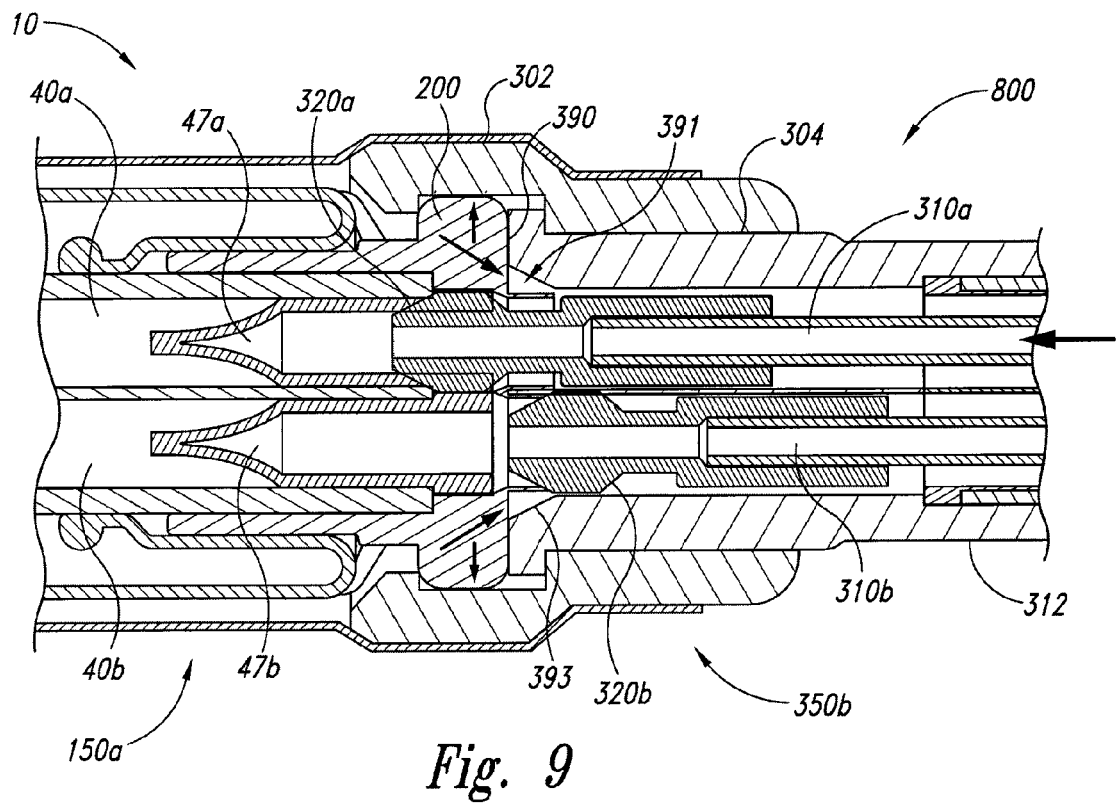
FIGS. 9-12 are cut-away views of the inflation device of FIG. 8 in various stages of engagement with the intragastric device in accordance with embodiments of the present technology.
Figure 10:
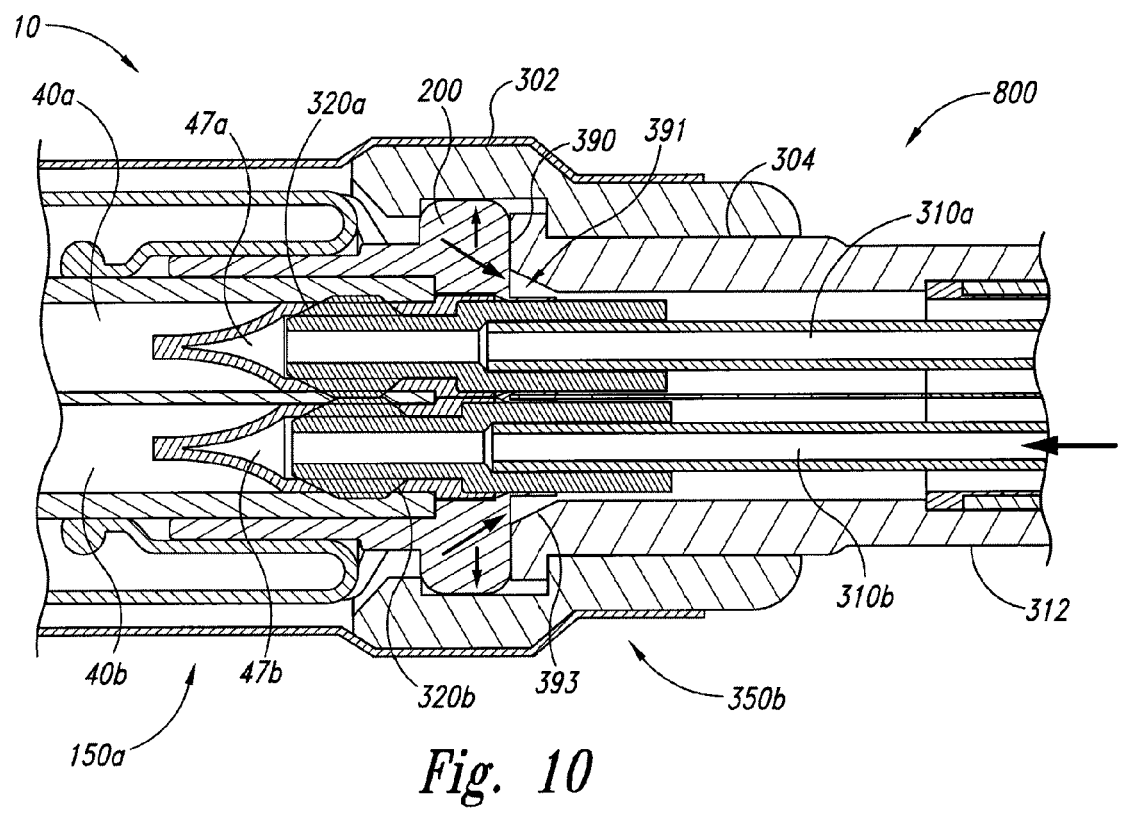

FIGS. 9-12 show the inflation device 800 of FIG. 8 in various stages of inserting the barbs 320 into the inflation ports 47 of the intragastric device 10. Referring to FIGS. 9-12 together, the intragastric device 10 may achieve an engaged state relative to inflation device 800. The outer detent 302 may be mated around a distal portion of the proximal cap 200, and the inner detent 304 may be mated against a proximal portion of the proximal cap 200. As shown in FIGS. 9 and 10, the first barb 320a and the second barb 320b may be mated within the corresponding first and second inflation ports 47a-b. In the engaged state, as shown in FIG. 10, the proximal cap 200 may expand due at least to the insertion of the barbs 320 into the corresponding inflation ports 47. The expansion of the proximal cap 200 may be against the outer detent 302, the inner detent 304, or the open space 391 defined by at least mating interface 390 and proximal cap 200.

In selected embodiments, engaging the intragastric device 10 with the inflation device 800 may be performed in situ within a gastric cavity of a patient. For example, the inflation device 800 may be attached to an intragastric device 10 that was previously deployed within the gastric cavity.

In other embodiments, engaging the intragastric device 10 with the inflation device 800 may be performed before insertion into a patient. For example, the intragastric device 10 and the inflation device 800 may be provided together in an engaged state or as a part of a kit of parts. Directions for use may further be provided. In the engaged state, the outer detent 302 may be mated around to a distal portion of the proximal cap 200, the inner detent 304 may be mated against a proximal portion of the proximal cap 200, and the first barb 320a and the second barb 320b may be mated within the first inflation port 47a and the second inflation port 47b, respectively. In the engaged state, the proximal cap 200 may be expanded.

The engaged intragastric device 10 and the inflation device 800 may be delivered to a gastric cavity. A fluid may be flowed to intragastric device 10. For example, the fluid may flow through at least one of the first handle 330a, the first tube 310a, the first barb 320a, the first inflation port 47a, the first inflation chamber 42a, the first inflation opening 32a, and the first balloon 30a. Similarly, the fluid may flow through at least one of the second handle 330b, the second tube 310b, the second barb 320b, the second inflation port 47b, the second inflation chamber 43b, the second inflation opening 33b, and the second balloon 30b. As such, at least one of the first balloon 30a and the second balloon 30b may be inflated to a desired volume.

In selected embodiments, the first balloon 30a and the second balloon 30b may be inflated simultaneously. Similarly, any number of balloons 30 may be inflated simultaneously corresponding to the number of separate inflation structures (e.g., handles 330, tubes 310, barbs 340, inflation ports 47, inflation chambers 42, and inflation openings 32). A plurality of inflation structures may reduce the total amount of time required to inflate the balloons 30 of intragastric device 10 by a factor corresponding to the number of inflation structures. For example, where N number of inflation structures are provided, the amount of time required to inflate the balloons 30 of the intragastric device 10 may be reduced by a factor of N. Additionally, because each balloon 30 includes at least one corresponding inflation structure, there is no need to attach a barb 320 to one inflation port 47, inflate, detach, and repeat the process with another inflation port 47.

Figure 11:
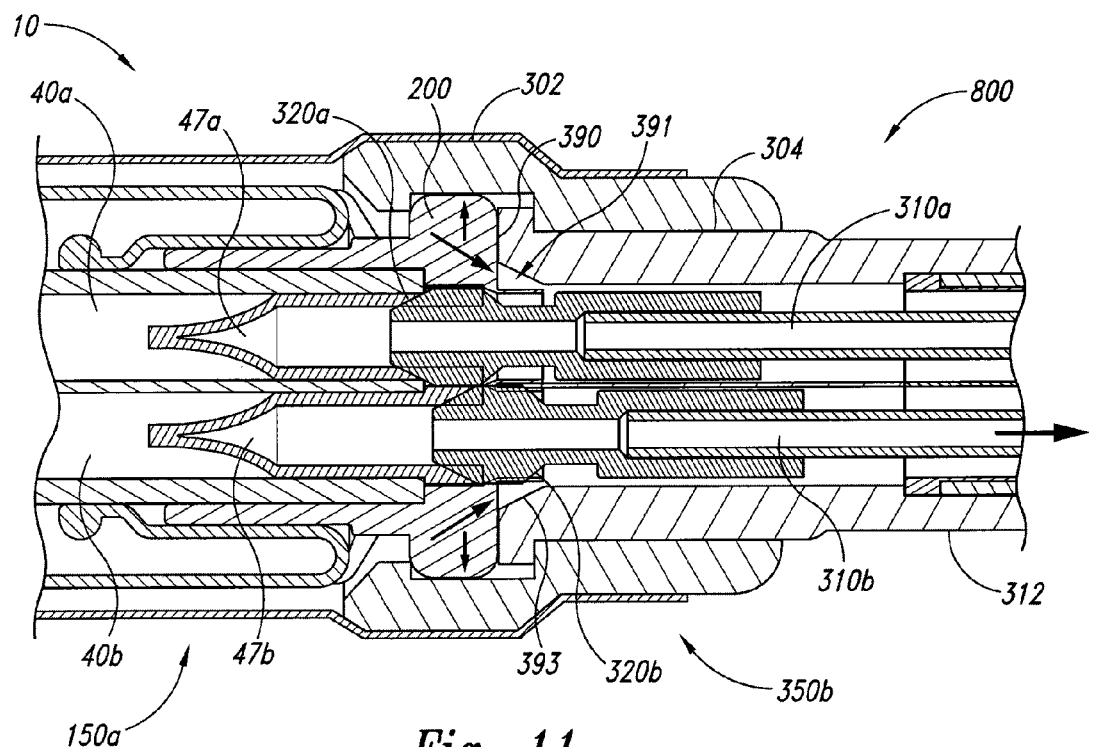
Figure 12:
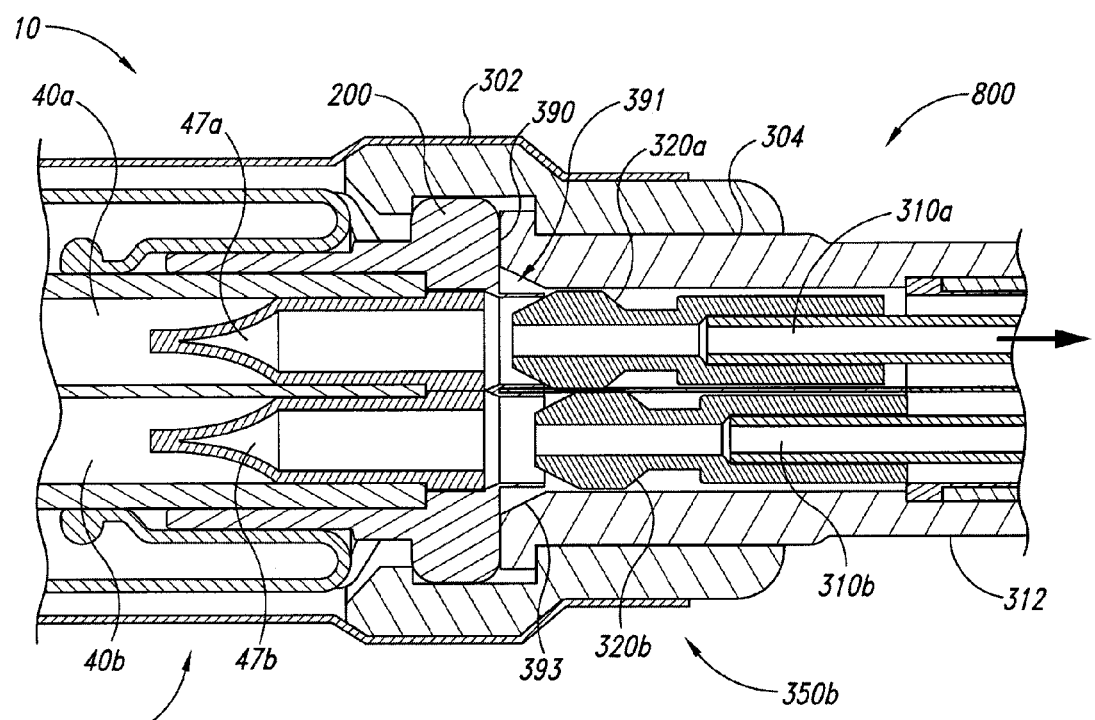

As shown in FIGS. 11 and 12, at least one of the first barb 320a and the second barb 320b may be retracted and removed from the corresponding inflation port 47. The open space 391 can facilitate withdrawal of the barbs 320 as it allows silicone material from the proximal cap 200 a place to go during barb withdrawal. In selected embodiments, a user may feel tactile feedback as each barb 320 moves out of the proximal cap 200. A user may also hear an audible feedback when the barb stops against the inner detent 304 if such a stop is provided, especially when the barb 320 stops against the inner detent 304. Accordingly, the proximal cap 200 may contract due to the removal of at least one of the first barb 320a and the second barb 320b. Such contraction may result in lower forces applied by the proximal cap 200 on the outer detent 302 or the inner detent 304. Therefore, the force required to disengage the outer detent 302 and/or the inner detent 304 from the proximal cap 200 may be reduced once the proximal cap 200 has contracted.

To disengage and separate the inflation device 800 from the intragastric device, the outer detent 302 may be removed from around the proximal cap 200 and the inner detent 304 may be removed from against the proximal cap 200. In selected embodiments, such separation of the inflation device 800 from the intragastric device 10 can result from the application of lateral forces. For example, the inflation device 800 may be advanced against the inflated gastric device 10, causing it to distort or rotate. The distorted shape or rotation of intragastric device 10 may cause a lateral force to be applied at the engagement location of the intragastric device 10 and the inflation device 800, causing it to buckle at the engagement location. Such forces may exceed the forces maintaining engagement. As described above, the forces maintaining engagement can be reduced after removal of the first barb 320a and/or the second barb 320b or by the mating interface 390. The reduction of this force may likewise reduce the force placed on the gastric wall supporting such actions. The body of the inflation device 800 may provide an opposing force to retract the barbs 320 such that the inserted barbs 320 do not exceed engagement forces, but with the removed barbs 320 it does exceed engagement forces. This allows for secure placement as well as very little to no pull force on removal of the inflation device 800.

In other embodiments, the inflation device 800 may be separated from the intragastric device 10 by opposing forces. A tension force may be provided by retracting the inflation device 800 at a second end thereof. An opposing force against the intragastric device 10 may be provided by the gastroesophageal junction. The junction may provide such a force after the balloon(s) 30 of intragastric device 10 are inflated such that a diameter thereof exceeds the diameter of the gastroesophageal junction. When force is applied from the gastroesophageal junction, it is inherent that a substantially equal tensile force applies to the engagement location of the inflation device 800. Reduction of the force required to disengage inflation device 800 from intragastric device 10 may be beneficial in that the force applied to and from the gastroesophageal junction is reduced. Accordingly, trauma to the gastroesophageal junction is likewise reduced.

In further embodiments, a force may be applied to the intragastric device 10 from another device that holds the intragastric device 10 in place relative to the retraction of the inflation device 800. For example, a rigid or partially rigid structure may hold the intragastric device 10 in place while the inflation device 800 is retracted.

Figure 13:
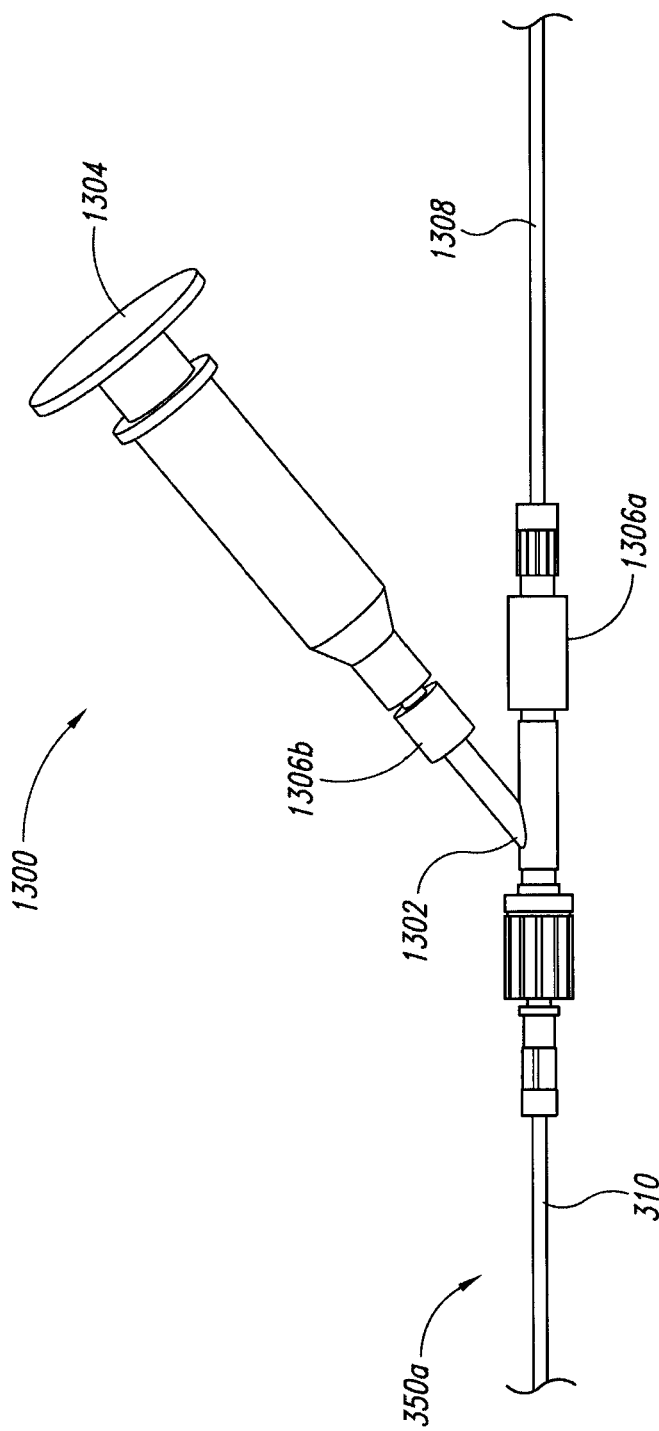
FIG. 13 is a side elevational view of an inflation assembly in accordance with an embodiment of the present technology.

FIG. 13 is a side elevational view of a proximal portion of an inflation assembly 1300 in accordance with an embodiment of the present technology. The inflation assembly 1300 can be coupled to the inflation devices 300 and 800 described above, and can be used to inject or otherwise introduce fluid into the intragastric device 10 (FIGS. 1-4). For example, FIG. 13 shows one of the tubes 310 at the proximal portion 350a of the intragastric device 300 or 800 coupled to a connector 1302 of the inflation assembly 1300. The connector 1302 can place a syringe and/or other fluid injection device 1304 in fluid communication with the tube 310. In the illustrated embodiment, for example, the connector 1302 is a Y-connector. In other embodiments, inflation assembly 1300 can include other suitable connectors 1302 that join the fluid injection device 1304 with the tubes 310. In operation, the fluid injection device 1304 can receive fluids and introduce them to the intragastric device 10 through the tubes 310. In selected embodiments, the fluid injection device 1304 can be used to introduce specific fluids into the balloons 30, such as mineral oils, antimicrobial agents, and/or other desired fluids or materials. The fillant fluid can be introduced into the balloons 30 through the fluid injection device 1304 and/or from a different site in fluid communication with the tubes 310. For example, as shown in FIG. 13, a fluid line 1308 (e.g., an IV line) can connect to one or more containers (e.g., a saline bag) that store the desired quantity of fluid for each balloon 30.

As further shown in FIG. 13, the inflation assembly 1300 can include one or more valves 1306 (identified individually as a first valve 1306a and a second valve 1306b) that regulate the direction of the fluid. For example, the valves 1306 can be one-way check valves to prevent backflow of the fluid as it enters the inflation assembly 1300. In the embodiments illustrated in FIG. 13, the first valve 1306a is positioned in line with the tubes 310 and the second valve 1306b is positioned in line with the fluid injection device 1304 to prevent backflow from each site of fluid entry. In other embodiments, one or more other valves 1306 can be included in the inflation assembly 1300 to regulate fluid entry and/or exit.

Additionally, the inflation assembly 1300, the inflation devices 300 and 800, and/or the intragastric device 10 described above can include features that reduce or prevent the mitigation of bacteria into the intragastric device 10 during or after implantation, inflation, deflation, and/or removal procedures. For example, the inflation assembly 1300 and the intragastric device 10 can include features that prevent bacteria from entering the balloons 30, and/or prevent bacteria from growing inside the balloons 30 during and after implantation. These features can prevent detrimental expansion of the balloons 30 caused by bacterial growth and its by-products (e.g., gas), reduce the likelihood of infection, and/or otherwise decrease failure of the intragastric device 10.

In selected embodiments, for example, components of the intragastric device 10, the inflation devices 300 and 800, the inflation assembly 1300, and/or associated devices (e.g., the delivery catheter, secondary inflation lines, syringes, containers, etc.) can be sterilized. The individual components of the inflation assembly 1300, the intragastric device 10, and/or other related tools and devices may be stored within a sterile kit as individual sterilized components. A sterile area or field can be used for set-up, implantation, and/or removal of the intragastric device 10. For example, associated devices can be attached to the inflation devices 300 and 800 on a sterile device tray, card, and/or other sterile working space before implantation. This sterile field can be packaged with the inflation devices 300 and 800, intragastric device 10, and/or inflation assembly 1300. Additionally, a cover (e.g., a hood, a cap) can encase connection sites (e.g., lures), the handles 330, related injection lines, fluid insertion containers 1304, and/or other components before implantation of the intragastric device 10. These covers can maintain the sanitation of the inflation devices 300 and 800, intragastric device 10, the inflation assembly 1300, and/or associated devices during implantation and inflation procedures. For example, covers can be pre-attached to portions (e.g., connection sites) of the inflation devices 300 and 800, intragastric device 10, and/or the inflation assembly 1300, such that the covered portion remains sanitized.

In other embodiments, the intragastric device 10, the inflation devices 300 and 800, the inflation assembly 1300, and/or portions thereof can be pre-attached before implantation such that the joined components can be sterilized together. For example, the inflation assembly 1300 can be pre-attached to the tubes 310. As another example, the inflation devices 300 and 800 can be pre-attached to the intragastric device 10.

In further embodiments, the inflation devices 300 and 800, the intragastric device 10, and/or associated devices can be comprised at least partially of materials with anti-microbial agents or other anti-bacterial features. The balloons 30, for example, can be made from a diphenyl loaded material. Additionally, the balloons 30 can be pressurized to reduce bacteria ingress.

The balloons 30 can also be filled with bacteriostatic fillants to prevent bacteria from growing within the balloons 30. For example, a sterile 0.9% sodium chloride solution bacteriostatic may be used as a fillant. Bacteriostatic agents can also be incorporated directly into the fillant. In selected embodiments, a bacteriostatic sealant, such as mineral oil with preservatives (e.g., tacophenol) can be used to kill expected bio-burden within the balloons 30.

In further embodiments, the inflation devices 300 and 800, the intragastric device 10, and/or other associated delivery and inflation devices can include other features to limit bacterial growth within the balloons 30. In selected embodiments, bacterial food sources can be reduced or eliminated. For example, powdered food sources (e.g. corn starch) on the intragastric device 10 and/or the inflation devices 300 and 800 may be replaced with sodium bicarbonate that is a less accessible carbon food source and creates a pH environment that is not favorable for some intragastric microbes. In other embodiments, a surface treatment (e.g., silicone dispersion) may be applied to interior portions of the balloons 30 to fill open pores in the balloon material. Lubricants (e.g., mineral oil) can also be injected inside the balloons 30 to fill porous portions. Inert and/or bacteriostatic dusting powder (e.g., zinc oxide, amoxicillin, barium sulfate, etc) can also be used within or over the balloons 30.

From the foregoing, it will be appreciated that specific embodiments of the technology have been described herein for purposes of illustration, but that various modifications may be made without deviating from the spirit and scope of the technology. For example, the intragastric device 10 shown in FIGS. 1-4 includes two balloons and the inflation devices 300 and 800 of FIGS. 5-12 include two corresponding inflation lines. However, other embodiments can include multiple inflation lines for individual balloons 30 to decrease inflation time. Certain aspects of the new technology described in the context of particular embodiments may be combined or eliminated in other embodiments. For example, the intragastric devices described above include balloons, but the intragastric devices can include other inflatable, elastic space-fillers. Additionally, the methods of engaging and separating the inflation device 800 from the intragastric device 300 described above with reference to FIGS. 8-12 can similarly apply to the inflation device 300 of FIG. 7. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A system, comprising:
an intragastric device including an inflatable balloon, a proximal cap having a flanged section, and an inflation port at a proximal portion of the intragastric device; and
an inflation device comprising—
  an outer detent at a distal portion of the inflation device configured to connect over the proximal cap of the intragastric device;
  an inner detent having a mating interface; and
  at least one tube fluidly connecting a handle at a proximal portion of the inflation device to a barb at the distal portion of the inflation device, the barb having a cross-sectional dimension greater than a cross-sectional dimension of the inflation port of the intragastric device when the inflation port is unengaged from the barb, wherein the barb is configured to expand the proximal cap when the barb is inserted into the inflation port such that the flanged section of the proximal cap expands into the outer detent.
2. The system of claim 1 wherein the barb is configured to mate within the inflation port of the intragastric device.

3. The system of claim 2 wherein the inflation port is fluidly connected to the inflatable balloon of the intragastric device.

4. The system of claim 1 wherein the barb is longitudinally advanceable relative to at least one of the outer detent and the inner detent.

5. The system of claim 1 wherein the mating interface is configured to leave an open space when the inner detent mates with the proximal cap.

6. The system of claim 5 wherein the open space is defined by the mating interface and the proximal cap.

7. The system of claim 5 wherein the mating interface is configured to allow at least a portion of the proximal cap to expand into the open space.

8. The system of claim 5 wherein the open space is proximal to a distal end surface of the inner detent and facing the barb.

9. The system of claim 1 wherein the mating interface includes a chamfered portion that defines an open space between the barb and the inner detent.

10. The system of claim 1 wherein the barb is configured to cause the proximal cap to contract when not inserted within the inflation port.

11. The system of claim 1 wherein the outer detent is configured to mate with a distal portion of the proximal cap.

12. The system of claim 1 wherein the inner detent is at least partially within the outer detent.

13. A system, comprising:
an intragastric device including a proximal cap and an inflation port at the proximal cap; and
an inflation device comprising—
a tube extending from a proximal portion of the inflation device to a distal portion of the inflation device, the tube having a handle at the proximal portion and a barb at the distal portion, wherein the barb has a cross-sectional dimension greater than a cross-sectional dimension of the corresponding inflation port of the intragastric device;
an inner detent over the barb, the inner detent having a mating interface; and
an outer detent over the inner detent, the outer detent being configured to attach over the proximal cap of the intragastric device, wherein the tube is longitudinally advanceable relative to at least one of the inner and outer detents, and
wherein a proximal portion of the proximal cap is configured to expand radially outward into engagement with the outer detent when the barb is inserted into the inflation port.

14. The system of claim 13 wherein the mating interface includes a chamfered portion.

15. The system of claim 14 wherein the chamfered portion is adjacent to the barb, and wherein the proximal cap and the chamfered portion define an open space adjacent to the barb.

16. The system of claim 13 wherein a portion of the mating interface defines an open space when the inner detent mates with the proximal cap.

17. The system of claim 13 wherein the tube is a first tube, the handle is a first handle, the barb is a first barb, the inflation port is a first inflation port, and wherein:
the intragastric device further comprises a second inflation port, wherein the first and second inflation ports are fluidly connected to a first balloon and a second balloon, respectively, of the intragastric device; and
the inflation device comprises a second tube extending from the proximal portion of the inflation device to the distal portion of the inflation device, the second tube having a second handle at the proximal portion and a second barb at the distal portion, wherein the second barb has a cross-sectional dimension greater than a cross-sectional dimension of the second inflation port of the intragastric device.

* * * * *